United States Patent [19]

Friese et al.

[11] Patent Number: 5,314,604
[45] Date of Patent: May 24, 1994

[54] SENSOR ELEMENT FOR LIMIT CURRENT SENSORS TO DETERMINE THE LAMBDA-VALUE OF GAS MIXTURES

[75] Inventors: Karl-Hermann Friese, Leonberg; Werner Gruenwald, Gerlingen; Hans-Martin Wiedenmann, Stuttgart, all of Fed. Rep. of Germany

[73] Assignee: Robert Bosch GmbH, Stuttgart, Fed. Rep. of Germany

[21] Appl. No.: 39,135

[22] PCT Filed: Sep. 21, 1991

[86] PCT No.: PCT/DE91/00752

§ 371 Date: Apr. 12, 1993

§ 102(e) Date: Apr. 12, 1993

[87] PCT Pub. No.: WO92/07252

PCT Pub. Date: Apr. 30, 1992

[30] Foreign Application Priority Data

Oct. 12, 1990 [DE] Fed. Rep. of Germany ....... 4032436

[51] Int. Cl.$^5$ ............................................. G01N 27/26
[52] U.S. Cl. ................................. 204/410; 204/412; 204/415; 204/424; 204/426; 204/429
[58] Field of Search ............... 204/410, 412, 415, 424, 204/426, 427, 429

[56] References Cited

U.S. PATENT DOCUMENTS

| | | | |
|---|---|---|---|
| 4,732,663 | 3/1988 | Kato et al. | 204/426 |
| 4,818,363 | 4/1989 | Bayha et al. | 204/426 |
| 4,824,549 | 4/1989 | Hamada et al. | 204/410 |
| 4,839,018 | 6/1989 | Yamada et al. | 204/425 |
| 5,098,549 | 3/1992 | Friese et al. | 204/425 |
| 5,137,615 | 8/1992 | Friese et al. | 204/425 |

FOREIGN PATENT DOCUMENTS

| | | |
|---|---|---|
| 0142993B1 | 5/1985 | European Pat. Off. . |
| 0142993A1 | 5/1985 | European Pat. Off. . |
| 0188900 | 7/1986 | European Pat. Off. . |
| 0194082 | 9/1986 | European Pat. Off. . |
| 3206903 | 9/1983 | Fed. Rep. of Germany . |
| 3527051C2 | 4/1986 | Fed. Rep. of Germany . |
| 3537051A1 | 4/1986 | Fed. Rep. of Germany . |
| 3543759 | 7/1986 | Fed. Rep. of Germany . |
| 3728618 | 3/1988 | Fed. Rep. of Germany . |
| 3728289 | 8/1988 | Fed. Rep. of Germany . |
| 3744206 | 8/1988 | Fed. Rep. of Germany . |
| 3809154 | 12/1988 | Fed. Rep. of Germany . |
| WO90/04171 | 4/1990 | PCT Int'l Appl. . |
| WO90/06506 | 6/1990 | PCT Int'l Appl. . |
| WO90/10862 | 9/1990 | PCT Int'l Appl. . |

Primary Examiner—John Niebling
Assistant Examiner—Bruce F. Bell
Attorney, Agent, or Firm—Spencer, Frank & Schneider

[57] ABSTRACT

A sensor element for broad band sensors to determine the λ-value of gas mixtures is suggested. This sensor element can be manufactured in ceramic-sheet and screen-printing technology and is provided in the diffusion gap (7) downstream from a pair of pump electrodes (8,8″), arranged on both sides of the diffusion gasp (7), with a Nernst electrode (9) which functions as an exhaust gas electrode. Due to this arrangement of the Nernst electrode (9), it is possible in a simple manner to effectively protect the pump cell formed by the interior pump electrodes (8,8′) from overload and to prevent falsification of the sensor signal.

7 Claims, 2 Drawing Sheets

SENSOR ELEMENT FOR LIMIT CURRENT SENSORS TO DETERMINE THE LAMBDA-VALUE OF GAS MIXTURES

STATE OF THE ART

The point of departure for the present invention is a sensor element according to the species defined in the main claim. These types of sensor elements, which operate on the diffusion limit current principle, measure the diffusion limit current while a constant voltage is applied to the two electrodes of the sensor element. In an exhaust gas resulting from combustion processes, this current is dependent on the oxygen concentration as long as the diffusion of gas to the pump electrode determines the speed of the occurring reaction. It is known to construct these types of sensors, which operate on the polarographic measuring principle, in such a way that both anode and cathode are exposed to the gas to be measured, with the cathode providing a diffusion barrier in order to achieve a performance in the diffusion limit current region.

The known limit current sensors generally serve to determine the λ-value of gas mixtures, which refers to the ratio "total oxygen/oxygen required for the complete combustion of fuel" of the air/fuel mixture combusted in a cylinder, with the sensors indicating the oxygen content of the exhaust gas via a limit current measurement, with a pump voltage lying in a predetermined range.

Due to a simplified and cost-effective production method, it has been found to be advantageous in practice in recent years to produce sensor elements by means of ceramic-sheet and screen-printing technology.

In a simple and efficient manner, it is possible to produce planar sensor elements starting with oxygen-conducting solid electrolytes, for example, of stabilized zircon dioxide, in the shape of platelets or sheets, with the electrolytes each being coated with an interior and exterior pump electrode and the associated conductor paths. In this case, the interior pump electrode is advantageously disposed in the edge region of a diffusion channel through which the measuring gas is supplied and which serves as gas diffusion resistance.

Sensor elements and detectors are also disclosed in DE-OS (unexamined published patent application) 3,543,759 and EP 0,142,993, 0,188,900, and 0,194,082 which have in common that each is provided with a pump cell and a sensor cell, which comprise two platelet or sheet-shaped oxygen-conducting solid electrolytes, two electrodes arranged thereon, and a common diffusion channel.

One drawback of the sensor elements of the type described is that the forward portion of the interior pump electrode facing the supplied measuring gas is more heavily used than the rearward portion of the pump electrode facing away from the supplied measuring gas. This results in high polarization of the electrodes which requires a high pump voltage. The latter, in turn, involves the danger of the electrolyte disintegrating in the region of the interior pump electrode.

In order to overcome this drawback, it is known from DE-OS 3,728,618 to arrange at least two interior pump electrodes in the diffusion channel of a sensor element for limit current sensors. This results in a marked reduction in the disadvantageous electrode polarization which easily occurs in sensor elements having only one interior pump electrode. At the same time, improved utilization of the noble metal required for the configuration of the pump electrode is achieved.

European Patent EP 0,194,082 also discloses a sensor element for determining the concentration of a gas component in gases, in particular, the exhaust gases from internal combustion engines. This sensor element comprises essentially a pump cell including two pump electrodes and a sensing cell including two further electrodes. However, construction of this sensor element is comparatively expensive, involving the impression of an auxiliary pump current on the exhaust gas side of the Nernst cell electrode and resulting in a comparatively high oxygen partial pressure both above the cathode of the pump cell and above the exhaust gas side of the Nernst cell electrode.

ADVANTAGES OF THE INVENTION

By contrast, the sensor element according to the present invention, having the characterizing features of the main claim, has the advantage of being relatively easily manufactured and effectively protects the pump cell of the sensor element from overload, so that a significantly improved service life of the sensor element is achieved. The essential characteristic of the sensor element according to the invention is thus the arrangement of a Nernst electrode in the diffusion gap and downstream of a dual pump electrode on both sides of the diffusion gap. The sensor element according to the invention is thus provided with a diffusion gap which is widened in the direction of the Nernst electrode forming the air reference channel for the exhaust gas electrode. The diffusion gap in this case is advantageously provided with a porous filling acting as a diffusion barrier. In case of a sensor element according to the invention, the oxygen partial pressure at the Nernst electrode in the diffusion gap in the stationary state cannot be greater than that at the pump electrode. The pump cell can therefore not be regulated for pump currents which are too high on the basis of excessive oxygen partial pressure on the Nernst electrode. The measured voltage of the Nernst electrode is not falsified by a load on the pump current, because it is not short-circuited to the pump electrode in the diffusion gap. On account of the dual pump electrode, it is ensured that $(PO_2)_{Nernst} \approx (PO_2)_{pm}$.

According to an advantageous modification of the invention, the air reference electrode of the Nernst cell is arranged in the air reference channel.

According to a further advantageous modification of the invention, the air reference electrode of the Nernst cell is arranged below the exhaust gas electrode of the Nernst cell and it is provided with a porous cover for the admission of air from the air reference channel. If the exterior electrodes are additionally advantageously enlarged in relation to the interior pump electrodes, their surfaces may, advantageously, be up to three times as large as the surface of the interior pump electrodes. It is further possible to advantageously arrange a porous cover layer above the exterior pump electrode.

It is possible to use the sensor element according to the invention in broad band sensors instead of prior art sensor elements having a planar structure, and to build it as such into a conventional sensor housing, for example, of the type disclosed in DE-OS 3,206,903 and 3,537,051, and to use it for measuring fuel/air ratios in exhaust gases.

DRAWING

Figure 1A:
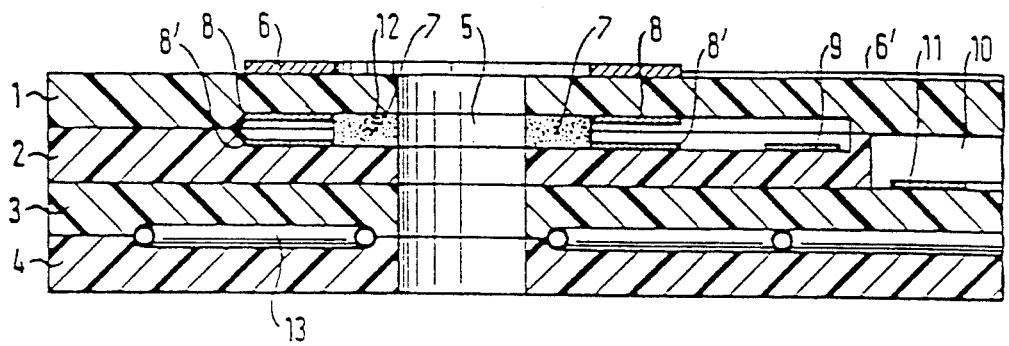
FIG. 1a is an enlarged sectional view of a sensor element according to the invention.

FIG. 1A is a schematic, greatly enlarged sectional view of an advantageous embodiment of a sensor element according to the invention which can be manufactured by means of ceramic-sheet and screen-printing technology. It essentially comprises four laminated solid electrolyte sheets, 1, 2, 3 and 4, including the punched-out central measuring gas supply opening 5; an annular exterior pump electrode 6, which is arranged around the measuring gas supply opening 5; interior pump electrodes 8, 8' facing one another and also arranged annularly about the measuring gas supply opening 5 in diffusion channel 7; an exhaust gas electrode 9 and an air reference electrode 11, arranged in air reference channel 10, which, together with the exhaust electrode, forms a Nernst cell; the porous tunnel filling 12 upstream of interior pump electrodes 8, 8'; and finally, a heater 13. Annular electrodes 6, 8 and 8', which are exposed to the measuring gas, are connected to conductor paths; for example, electrode 6 is connected to conductor path 6', with an insulating layer, for example, an $Al_2O_3$ layer, being arranged below the conductor paths. The conductor paths are connected to a voltage source which is not shown, for example, a battery with an operational voltage in the 0.5 to 1.0 volt range whose polarity is set as a function of the $\lambda$-value of the exhaust gas. The exterior pump electrode and the associated conductor path are advantageously covered with a porous cover layer, for example, of magnesium spinel.

Figure 1B:
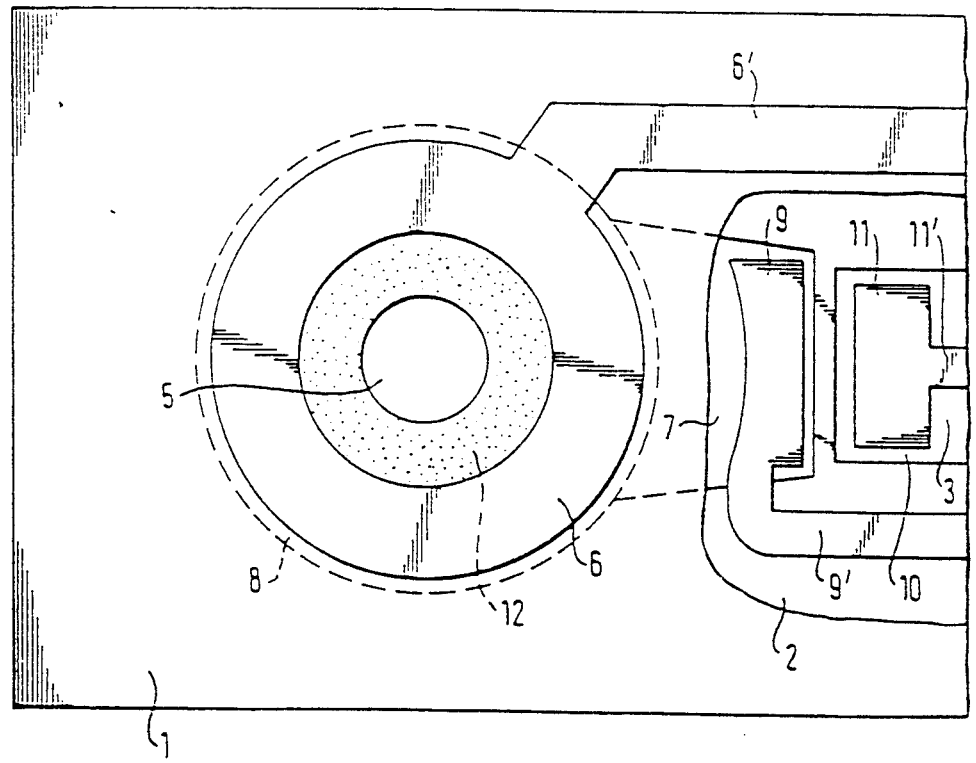
FIG. 1b is an enlarged top view of a sensor element according to the invention.

FIG. 1B is a schematic, greatly enlarged top view of the sensor element according to FIG. 1A, including additional conductor paths 9' and 11'.

Figure 2A:
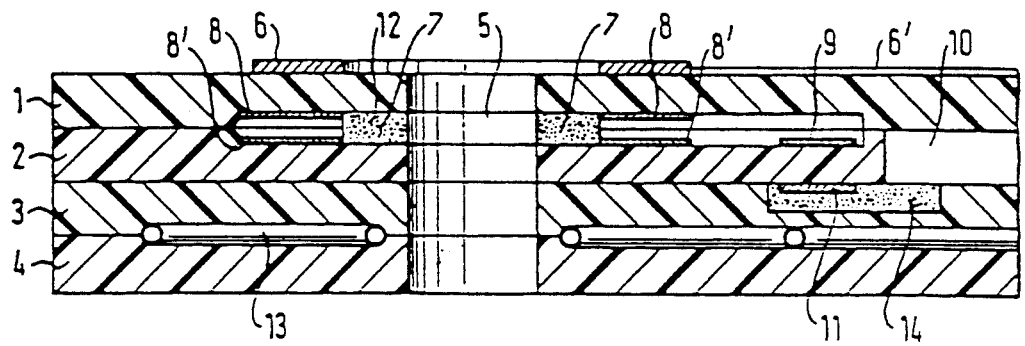
FIG. 2a is an enlarged sectional view of another embodiment of a sensor element according to the invention.

FIG. 2A is a further schematic, greatly enlarged sectional view of a second embodiment of a sensor element according to the invention which can be produced by ceramic-sheet or screen-printing technology. It differs from the embodiment shown in FIGS. 1A and 1B merely in that air reference electrode 11 is not arranged in air reference channel 10, but below the exhaust electrode 9. In this case, air reference electrode 11 is provided with a porous cover 14, which allows air to enter from air reference channel 10.

Figure 2B:
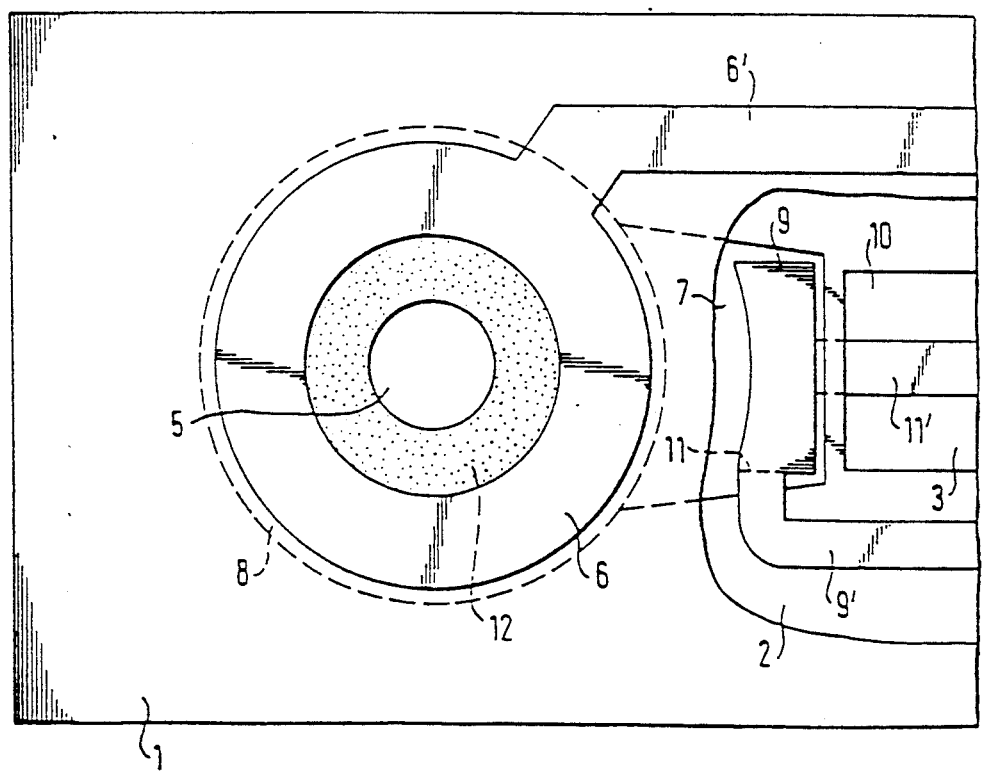
FIG. 2b is an enlarged top view of another embodiment of a sensor element according to the invention.

FIG. 2B is a schematic, greatly enlarged top view of the sensor element according to FIG. 2A.

Oxygen ion-conducting solid electrolytes suitable for the production of sensor elements according to the invention are particularly those based on $ZrO_2$, $HfO_2$, $CeO_2$ and $ThO_2$. The use of platelets and sheets of yttrium-stabilized zirconium dioxide (YSZ) has proved to be particularly advantageous. In this case, the thickness of the platelets and sheets is preferably 0.25 to 0.3 mm.

The pump electrodes are preferably made of a metal from the platinum group, in particular, platinum, or from metal alloys from the platinum group or alloys of metals from the platinum group in combination with other metals. They advantageously contain a ceramic supporting structure material, such as, for example, YSZ powder, preferably in a volume percentage of approximately 40 volume %. They are porous and have a thickness of preferably 8 to 15 $\mu$m. The conductor paths associated with the pump electrodes preferably also comprise platinum or a platinum alloy of the described type. Pump electrodes and conductor paths can be applied to the solid electrolyte carriers by means of known methods, such as, for example, screen printing. An insulating layer, for example, of $Al_2O_3$, is generally provided between the conductor path connecting the exterior pump electrode with a voltage source, which is not shown in the drawing, and the solid electrolyte carrier. The layer may have a thickness, for example, of approximately 15 $\mu$m. Joining of the individual sheets or platelets which form the sensor element can be performed by a method which is customary in ceramic-sheet and screen-printing technology in which the sheets are joined together and are heated to approximately 100° C. In this case, the diffusion channel can be prepared at the same time. The diffusion channel is advantageously made by means of punching a slot into sheet 2 or by means of thick-film technology, for example, by means of a theobromine screen-print layer, with the theobromine being evaporated in the subsequent sintering process. To produce the diffusion channel it is also possible to use, for example, thermal carbon black powders, which burn off during the sintering process, or ammonium carbonate, which evaporates.

If the diffusion channel is advantageously provided with a porous filling, it is possible, for example, to use, instead of a theobromine screen printing layer a layer of theobromine or another material that is able to evaporate or burn and a material that does not yet not sinter densely at the sintering temperature of the solid electrolyte substrate, for example, a coarse-grained $ZrO_2$, Mg spinel or $Al_2O_3$ having a grain size of, for example, 10 $\mu$m.

EXAMPLE

To produce a sensor element of the type shown schematically in FIGS. 1A and 1B, sheets made of yttrium-stabilized zirconium dioxide having a layer thickness of 0.3 mm were used. Application of the platinum pump electrodes and the electrodes of the Nernst cell, i.e., the exhaust gas electrode and the reference electrode, to the carrier sheets was performed according to known screen print technology, with a 20 $\mu$m thick $Al_2O_3$ insulating layer having previously been applied in the region of the conductor path of the exterior pump electrode to the surface of the carrier sheet carrying the exterior pump electrode. The annular pump electrodes had an exterior diameter of 2.8 mm and an interior diameter of 1.4 mm with a thickness of 12 $\mu$m. The conductor paths were made starting with the usual Pt-cermet paste containing 85 parts by weight Pt-powder and 15 parts by weight YSZ powder. The diffusion channel was made in thick-film technology by means of a theobromine screen-print layer, with the theobromine having been evaporated in the subsequent sintering process in a temperature range around 300° C., leaving behind an approximately 30 $\mu$m high and 1.3 mm deep annular gap. The sheets provided with the printed electrodes and conductor paths were laminated together with further sheets, using a printed-on heater. The punched-out central measuring gas supply opening had a diameter of 0.25 mm. The air reference channel was punched into sheet 2. Subsequent to printing the carrier sheets, i.e, after applying the electrodes, conductor paths, insulating layer and, if applicable, the cover layer, to the exterior pump electrode, the sheets were subjected after joining to a sintering process during which they were heated for approximately three hours to a temperature in a range of 1380° C.

The manufactured sensor elements were built into a sensor housing of the type disclosed in DE-OS 3,206,903 and 3,537,051 were used for measuring the fuel/air ratio in weak and rich exhaust gases.

We claim:

1. Sensor element for limit current sensors to determine the λ-value of gas mixtures, in particular, of exhaust gases from internal combustion engines; the sensor including an exterior and an interior pump electrode arranged on $O_2^-$ ion-conducting solid electrolyte sheet, with the interior pump electrode being arranged in a diffusion channel for the measuring gas and being short-circuited to a second interior pump electrode arranged in the diffusion channel, and the interior pump electrode and the exterior pump electrode being arranged annularly around the measuring gas supply, with the interior pump electrodes facing each other in the diffusion channel, characterized in that the diffusion channel contains a filling which acts as diffusion barrier and which is positioned in the direction of the incoming gas upstream of the interior pump electrodes and that an exhaust gas electrode and an air reference electrode form a Nerst Cell, wherein the exhaust gas electrode is arranged in the diffusion channel downstream from interior pump electrodes.

2. Sensor element according to claim 1, characterized in that the air reference electrode of the Nernst cell is arranged in an air reference channel.

3. Sensor element according to claim 1, characterized in that the air reference electrode of the Nernst cell is arranged below the exhaust gas electrode of the Nernst cell and is provided with a porous cover for air to enter from air reference channel.

4. Sensor element according to claim 1, characterized in that the air reference electrode is enlarged in relation to interior pump electrodes.

5. Sensor element according to claim 1, characterized in that a porous covering layer is arranged above the exterior pump electrode.

6. Sensor element according to claim 1, characterized in that it is manufactured in ceramic-sheet and screen-printing technology.

7. Sensor element according to claim 1, characterized in that it is provided with a heater.

* * * * *